United States Patent [19]

Sablayrolles et al.

[11] Patent Number: 5,028,605

[45] Date of Patent: Jul. 2, 1991

[54] 8-ALKYLAMINOIMIDAZO(1,2-A)PYRAZINES AND DERIVATIVES, THEIR PREPARATION AND THEIR APPLICATION IN THERAPY

[75] Inventors: Claire Sablayrolles; Pierre-Antoine Bonnet; Gérard Cros; Jean-Pierre Chapat; Maurice Boucard, all of Montpellier, France

[73] Assignee: L'Universite de Montpellier I, Montpellier, France

[21] Appl. No.: 364,428

[22] PCT Filed: Dec. 4, 1987

[86] PCT No.: PCT/EP87/00756

§ 371 Date: Jun. 2, 1989

§ 102(e) Date: Jun. 2, 1989

[87] PCT Pub. No.: WO88/04298

PCT Pub. Date: Jun. 16, 1988

[30] Foreign Application Priority Data

May 12, 1986 [FR] France ............................... 86 17164

[51] Int. Cl.$^5$ ................ C07D 487/04; A61K 31/495; A61K 31/535; A61K 31/54
[52] U.S. Cl. ............................ 514/228.5; 514/232.5; 514/233.2; 514/249; 544/58.6; 544/61; 544/117; 544/350
[58] Field of Search ................ 544/350, 58.6, 61, 117; 514/249, 228.5, 232.5, 233.2

[56] References Cited

U.S. PATENT DOCUMENTS 4,537,889 8/1985 Spitzer ................................ 544/350

FOREIGN PATENT DOCUMENTS 13914 8/1980 European Pat. Off. .
166609 1/1986 European Pat. Off. .

OTHER PUBLICATIONS

"Attorney's Dictionary of Patent Claims" (Aisenberg) vol. 1 (1988).

Primary Examiner—Mark L. Berch
Attorney, Agent, or Firm—Irwin M. Aisenberg

[57] ABSTRACT

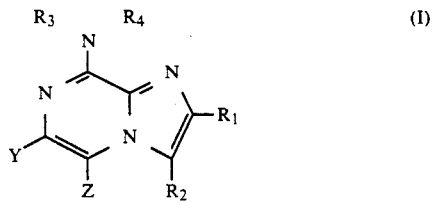

Novel 8-alkylamino-imidazo(1,2-a)pyrazines of formula (I) show advantages pharmacological activities. They can be used for medical products in human and veterinary therapy in the field of applications of antispasmodics, uterine relaxants, bronchodilators, cardiac analeptics and neurosedatives.

30 Claims, No Drawings

8-ALKYLAMINOIMIDAZO(1,2-A)PYRAZINES AND DERIVATIVES, THEIR PREPARATION AND THEIR APPLICATION IN THERAPY

The present invention relates to 8-alkylaminoimidazo[1,2-a]pyrazines and their derivatives, their preparation and their therapeutic application in human or veterinary medicine in the field of antispasmodics, uterine relaxants, bronchodilators, cardiac analeptics and neurosedatives.

Imidazo[1,2-a]pyrazines possessing advantageous pharmacological activities have already been described in the literature, for example in U.S. Pat. Nos. 4,507,294, 4,483,858, 4,376,772 and 4,242,344, in British patent No. 2,132,203, in European patents Nos. 0,013,914, 0,113,236 and 0,154,494 and in various publications such as those produced by ABIGNENTE, E. et al. Eur. J. Med. Chemistry, 1985, p. 79-85, 20 and SABLAYROLLES C. et al. J. Med. Chem., 1984 p. 206-212, 27.

The present invention encompasses the compounds corresponding to the formula:

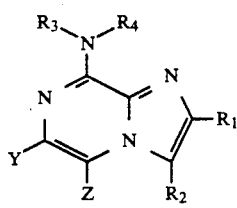

as well as the corresponding salts which are compatible with pharmaceutical application.

In this formula (I):

. Y and Z independently denote:
  a) a hydrogen atom,
  b) a halogen atom such as F, Cl, Br or I,
  c) $CO_2H$,
  d) CN,
  e) a linear or branched $C_1$-$C_5$ alkyl radical,
  f) a $C_1$-$C_5$ alkoxy radical,
  g) $CF_3$

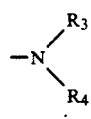 (h)

with $R_3$ and $R_4$ as defined below;

. $R_1$ and $R_2$, when they are independent, denote,
  a) a hydrogen atom,
  b) a halogen atom, such as F, Cl, Br or I,
  c) a linear or branched $C_1$-$C_5$ alkyl radical,
  d) a radical —$(CH_2)_n$—$CO_2R_5$, with $R_5$ denoting a $C_1$-$C_5$ alkyl radical and n being from 0 to 4,

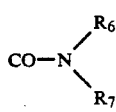 (e)

with $R_6$ and $R_7$ independently denoting a hydrogen atom, a linear or branched $C_1$-$C_5$ alkyl radical or an aryl radical, f) CN,

h) $NH_2$,
i) $CH_2Cl$,
j) $CH_2OH$,
k) $CF_3$,

m) —$NO_2$,
n) —NO,
o) a $C_3$-$C_6$ cycloalkyl radical,
p) an acyl radical,
q) a linear or branched $C_1$-$C_5$ alkylthio radical;

. $R_1$ and $R_2$, when they are linked to one another, denote —$CH_2$—$CH_2$—$CH_2$—$CH_2$—, . $R_3$ and $R_4$ independently denote:
  a) a hydrogen atom
  b) a linear or branched $C_1$-$C_5$ alkyl radical, capable of bearing one or more halogen atoms or a hydroxy, $N(C_1$-$C_4$ alkyl$)_2$, carbamoyl or $C_1$-$C_4$ alkoxy radical, either a $C_3$-$C_6$ cycloalkyl radical or a phenyl radical,
  c) a $C_1$-$C_5$ acyl radical,
  d) a furfuryl radical, . $R_3$ and $R_4$, linked to one another denote —$CH_2$—$CH_2$—$CH_2$—$CH_2$—$CH_2$ or —$CH_2$—$CH_2$—X—$CH_2$—$CH_2$— in which X denotes O or S.

The preferred compounds of the invention are those in which $R_3$ is a hydrogen atom, $R_4$ a hydrogen atom or a methyl or ethyl radical, $R_1$ a hydrogen atom or an ethyl carboxylate group, Y and Z denote either a hydrogen atom or a bromine atom and $R_2$ denotes either a bromine atom or a hydrogen atom. Among these compounds, there may be mentioned more especially the compound in which $R_3$=H, $R_4$=$CH_3$, Y=H, Z=H, $R_2$=Br and $R_1$=H, the compound in which $R_3$=H, $R_4$=$CH_3$, Y=Br, Z=H, $R_2$=H, $R_1$=H and the compound in which $R_3$=H, $R_4$=H, Y=Br, Z=H, $R_2$=Br and $R_1$=H.

The salts that are compatible with pharmaceutical application are the salts resulting from the neutralization of the basic compounds corresponding to the formula (I) with an acid. The acids employed are either inorganic or organic acids. As examples of such inorganic acids, halogen hydracids, such as hydrochloric acid, hydrobromic acid and hydriodic acid, phosphoric acid, sulfuric acid, and the like should be mentioned. As examples of organic acids, carboxylic acids such as acetic acid, maleic acid, succinic acid, citric acid, tartaric acid, oxalic acid, malic acid, pivalic acid, heptanoic acid, lauric acid, slaicylic acid, benzoic acid, glutamic acid, lactic acid, and the like and non-carboxylic acids such as isethionic acid and methane-sulfonic acid, should be mentioned. The salts of halogen hydracids, especially the hydrochlorides, the salts of maleic acid, especially the acid maleates, and the salts of methanesulfonic acid are preferred.

According to the invention, the compounds (I) may be prepared according to the reaction schemes 1 and 2 below, which employ known processes and which use known starting substances. The particular methods and the reaction sequences are derived from the specific nature of the substituents and their position.

One of the processes for producing the compounds (I) (scheme 1) consists in condensing a 2,3-diamino- or 3-alkylamino-2-aminopyrazine (II) containing the substituents Y and Z with an alpha-halocarbonyl compound (III).

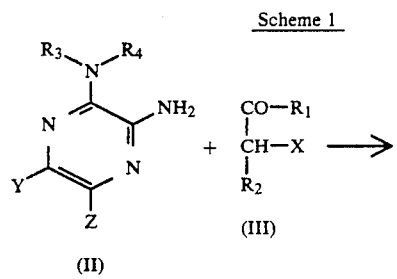

Another process (scheme 2) for producing the compounds (I) consists in carrying out a substitution reaction starting with an imidazo[1,2-a]pyrazine derivative, according to a traditional method, for example by the action of ammonia, alkylamines or a nitrogenous heterocycle on a halogenated derivative. The halogenated derivative used can be either a derivative halogenated at the 8-position (compound IV), or a derivative halogenated at the 5-position (compound V), the substitution reaction in this case being accompanied by a change in the position of substitution (telesubstitution). In the compounds of the formulae (IV) and (V), X denotes a chlorine or bromine atom.

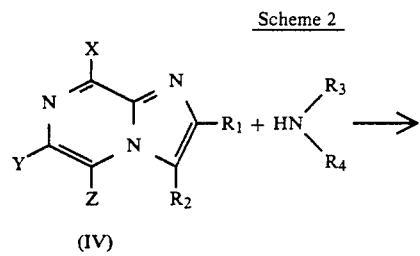

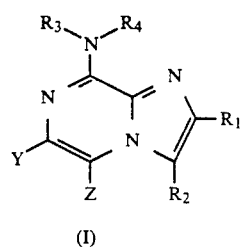

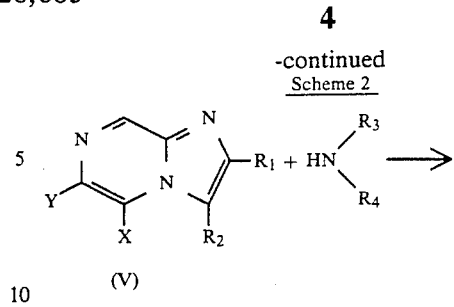

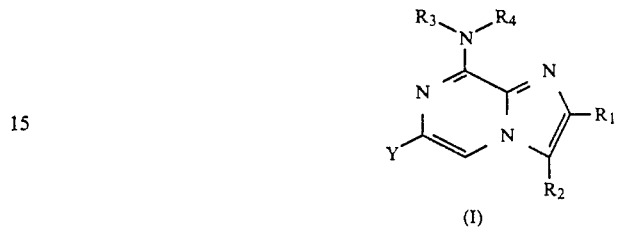

The halogenated derivatives (IV) possessing a halogen at the 8-position may in turn be obtained (scheme 3) from a substituted 2-amino-3-halopyrazine (VI) which is condensed with an alpha-halocarbonyl derivative (III).

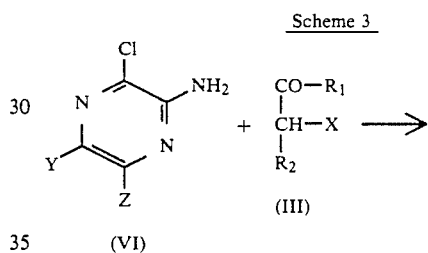

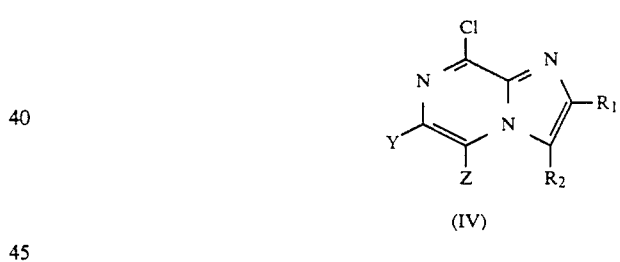

Another method for obtaining a compound of general formula (IV) possessing a chlorine atom at the 8-position consists in treating an imidazo[1,2-a]pyrazine with sulfuryl chloride. There is thus obtained, for example, from ethyl imidazo[1,2-a]pyrazine-2-carboxylate (VII), a mixture of ethyl trichloro- and 5,6,7,8 tetrachloroimidazo-[1,2-a]pyrazine-2-carboxylate (VIII) (scheme 4), in which the chlorine at the 8-position is the atom which may be most readily substituted by an amine of type:

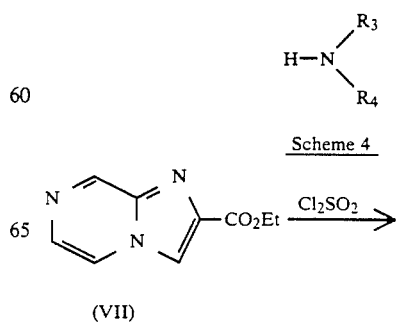

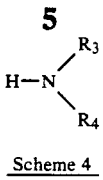

Scheme 4

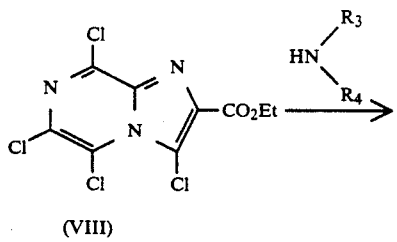

(VIII)

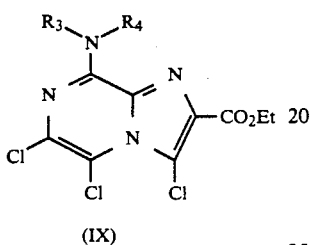

(IX)

The halogenated derivatives possessing a halogen atom at the 5-position (compound V) may be obtained according to the above process (scheme 3), replacing the compound (VI) by the compound (VI')

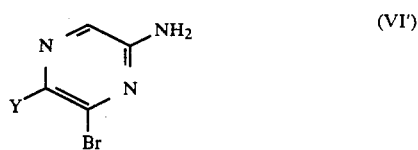

in which the halogen is, for example, a bromine atom, but also by direct halogenation (scheme 5) of a substituted imidazo[1,2-a]pyrazine possessing a hydrogen atom at the 5-position, using the usual reagents, for example bromine in ethanol or acetic acid, N-bromosuccinimide, and the like.

Scheme 5

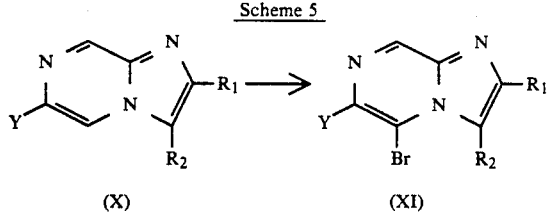

The 2-amino pyrazines (VI) and (VI'), the alphahalocarbonyl compounds (III) and the imidazo[1,2-a]pyrazines (VII) and (X) employed in the production methods described above are commercial products or products prepared from common starting substances by traditional methods known to those versed in the art.

The groups $R_1$, $R_2$, Y and Z of the general formula (I) of the compounds of the invention are provided by the starting compounds (VI), (VI'), (II) and (III) or are obtained after condensation to the corresponding substituted imidazo[1,2-a]pyrazine. For example, nucleophilic substitution reactions are carried out starting out with derivatives halogenated at the 3-, 5- and 6-positions, using traditional nucleophilic reagents ($CN^-$, $X^-$, $HNR_3R_4$, $RO^-$, $RS^-$, and the like); an ester group is converted to amide by the action of ammonia in concentrated aqueous solution, and then either to an amine by the action of sodium hypobromite or to a nitrile by dehydration using phosphorus oxytribromide. A chloromethyl group leads via the action of ammonia to an aminomethyl group, or via the action of an N-alkylamine to an N-alkylaminomethyl group.

In the same manner, different derivatives may be prepared from an imidazo[1,2-a]pyrazine by an electrophilic substitution reaction on the unsubstituted 3-position. A trifluoroalkylthio group is thereby obtained via the action of trifluoromethanesulfonylchloride and the sulfonamide derivative via the action of chlorosulfonic acid followed by thionyl chloride and an amine, such as methylamine, for example. Similarly, reaction of N-bromosuccinimide or N-chlorosuccinimide yields, respectively, the derivatives brominated or chlorinated at the 3-position. Perchloryl fluoride yields the derivative fluorinated at the 3-position. The action of nitrous acid prepared at the time of use or butyl nitrite gives the nitroso derivative. The nitro derivative results from the action of nitric acid in sulfuric medium.

The examples which follow are given by way of illustration and in no way imply limitation of the invention.

The analyses and the IR, NMR and MS spectra confirm the structure of the compounds.

EXAMPLE 1

3-Bromo-8-methylaminoimidazo[1,2-a]pyrazine

Stage preparation of imidazo[1,2-a]pyrazine

A mixture of 34 g (0.2 mol) of bromoacetaldehyde dimethyl acetal, 6,6 ml of concentrated aqueous HBr solution and 28 ml of distilled water is brought to reflux for one hour. After reaction, the mixture is alkalinized and extracted with ether. This organic phase is added to a solution of 19 g (0.2 mol) of aminopyrazine in 50 ml of dimethylformamide (DMF). The ether is removed by distillation and the mixture is maintained with stirring and under a stream of nitrogen for 12 hours. After reaction, the DMF is distilled off; the reaction medium is dissolved in 150 ml of anhydrous ethanol, and then brought to reflux for one hour. The alcohol is then removed by distillation; the residue is dissolved in water, alkalinized with $Na_2CO_3$ and extracted using dichloromethane. After chromatography on a neutral alumina column (eluant = anhydrous ether), 10.7 g (Yld = 45%) of imidazo[1,2-a]pyrazine (m.p. 84° C.) are obtained.

Stage B: preparation of 3,5-dibromoimidazo[1,2-a]pyrazine.

A solution of 12 ml of bromine in 10 ml of acetic acid is added dropwise to a solution of 6 g (50.5 mmol) of imidazo[1,2-a]pyrazine in 70 ml of acetic acid. The solution brought to reflux for one and a half hours is then evaporated under vacuum. The residue is then dissolved in water, alkalinized with $Na_2CO_3$ and extracted with dichloromethane. After chromatography on a neutral alumina column (eluant = anhydrous ether), 8,38 g (Yld = 60%) of 3,5-dibromoimidazo[1,2-a]pyrazine (m.p. 150° C.) are obtained.

Stage C: preparation of 3-bromo-8-methylaminoimidazo[1,2-a]pyrazine.

A mixture of 1 g (3,6 mmol) of 3,5-dibromoimidazo[1,2-a]pyrazine in 9 ml of a 40% strength aqueous methylamine solution is maintained with stirring for 12 hours. After evaporation under reduced pressure and chromatography on a silica column eluted with ether, 0.33 g (Yld=40%) of 3-bromo-8-methylaminoimidazo[1,2-a]pyrazine (m.p. 139° C.) is obtained.

By replacing, in Example 1 above, stage C, methylamine by:

ammoniacal alcohol, 8-amino-3-bromoimidazo[1,2-a]pyrazine (m.p. 239° C.) is obtained;
ethylamine, 3-bromo-4-ethylaminoimidazo[1,2-a]pyrazine (m.p. 82° C.) is obtained.

EXAMPLE 2

8-Morpholinoimidazo[1,2-a]pyrazine

Stage A: preparation of 6,8-dibromoimidazo[1,2-a]pyrazine

This derivative is obtained according to a technique identical to that of Example 1, stage A, by replacing 2-aminopyrazine by 2-amino-3,5-dibromooyrazine. 10 g (39.5 mmol) of this compound yield 5.47 g (Yld=50%) of 6,8-dibromoimidazo[1,2-a]pyrazine (m.p. 165° C.).

Stage B: preparation of 6-bromo-8-morpholinoimidazo[1,2-a]pyrazine

A solution of 1 g (3,6 mol) of 6,8-dibromoimidazo[1,2-a]pyrazine and 1 g (11.2 mmol) of morpholine in 15 ml of anhydrous ethanol is brought to reflux for 12 hours. After evaporation of the solvent and chromatography on an alumina column (eluant=$CH_2Cl_2$), 0.88 g (Yld=85%) of 6-bromo 8-morpholinoimidazo[1,2-a]pyrazine (m.p. 191° C.) is obtained.

Stage C: preparation of 8-morpholinoimidazo[1,2-a]pyrazine.

200 mg of palladium on charcoal (10% palladium) are added to a solution containing 0.5 g (1.77 mmol) of 6-bromo-8-morpholinoimidazo[1,2-a]pyrazine for 120 ml of anhydrous methanol and 2 g of potassium hydroxide. The mixture is hydrogenated at atmospheric pressure for 12 hours. The solution is filtered, concentrated and taken up with water; after extraction with dichloromethane and evaporation of the solvent, 0.34 g (92%) of 8-morpholinoimidazo[1,2-a]pyrazine (m.p. 127° C.) is obtained.

By replacing, in Example 2 above, stage B, morpholine by the different amines referred to in Table I below, the corresponding substituted 6-bromoimidazo[1,2-a]pyrazines, recorded in the same table, are obtained. Treatment of the products thereby obtained according to the process described in Example 2, stage C, yields the substituted imidazo[1,2-a]pyrazines referred to in Table I.

TABLE I

| Amines | Results of stage B | Result of Stage C |
|---|---|---|
| Ammoniacal alcohol | 8-amino-6-bromoimidazo[1,2-a]pyrazine (m.p. 210° C.) | 8-aminoimidazo[1,2-a]-pyrazine (m.p. 220° C.) |
| Methylamine | 6-bromo-8-methylaminoimidazo[1,2-a]pyrazine (m.p. 162° C.) | 8-methylaminoimidazo-[1,2-a]pyrazine (m.p. 96° C.) |

TABLE I-continued

| Amines | Results of stage B | Result of Stage C |
|---|---|---|
| Ethylamine | 6-bromo-8-ethylaminoimidazo[1,2-a]pyrazine (m.p. 99° C.) | 8-ethylaminoimidazo-[1,2-a]pyrazine (m.p. 98° C.) |
| Furfurylamine | 6-bromo-8-furfurlaminoimidazo[1,2-a]pyrazine (m.p. 164° C.) | 8-furfurylaminoimidazo-[1,2-a]pyrazine (m.p. = pasty) |

EXAMPLE 3

Ethyl 6-bromo-8-methylaminoimidazo[1,2-a]pyrazine-2-acetate

Stage A: preparation of 2-amino-5-bromo-3-methylaminopyrazine 1.55 g (50 mmol) of 40% strength aqueous methylamine solution is added to a solution of 2.53 g (10 mmol) of 3,5-dibromo-2-aminopyrazine in ethanol. The mixture is stirred in an autoclave at 130° C. for 17 hours. After evaporation of the solvent under reduced pressure, the product is purified by chromatography on a silica column (eluant=$CH_2Cl_2$, to which 3% of $CH_3OH$ has been added). 0.8 g (Yld=40%) of 2-amino-5-bromo-3-methylaminopyrazine (m.p. 121° C.) is obtained.

Stage B: preparation of ethyl 6-bromo-8-methylaminoimidazo[1,2-a]pyrazine-2-acetate.

2.03 g (10 mmol) of 2-amino-5-bromo-3-methylaminopyrazine are dissolved in 5 ml of dimethylformamide (DMF). A solution of 1.645 g(10 mmol) of ethyl (chloroacetyl)acetate in 5 ml of DMF is added dropwise with stirring. The mixture is maintained with stirring and under gentle reflux for 3 hours. The DMF is then evaporated off under reduced pressure and the residue, dissolved in 50 ml of anhydrous ethanol, is brought to reflux for one hour. After removal of the solvent, the residue is taken up with water, alkalinized and extracted with dichloromethane. After dehydration over anhydrous calcium chloride, the solvent is evaporated off under reduced pressure. The crude product is purified by chromatography on a silica column (eluant=dichloromethane to which 5% of methanol has been added). 0.4 g (Yld=30%) of ethyl 6-bromo-8-methylaminoimidazo[1,2-a]pyrazine-2-acetate (m.p. 104° C.) is obtained.

By replacing, in the Example 3 above, stage B, 2-amino-5-bromo-3-methylaminopyrazine by an equimolar amount of substituted 2-aminopyrazines and ethyl (chloroacetyl)acetate by ethyl bromopyruvate, the 8-aminoimidazo[1,2-a]pyrazine derivates appearing in Table II below are obtained.

For the final derivative listed in this Table II, only the replacement of 2-amino-5-bromo-3-methylaminopyrazine by the substituted 2-aminopyrazine is necessary.

TABLE II

| Substituted 2-aminopyrazines: | 8-Aminoimidazo[1,2-a]-pyrazine derivatives: |
|---|---|
| 2,3-diaminopyrazine | ethyl 8-aminoimidazo[1,2-a]-pyrazine-2-carboxylate (m.p. 230° C.). |
| 2,3-diamino-5-bromopyrazine | ethyl 8-amino-6-bromoimidazo[1,2-a]pyrazine-2-carboxylate (m.p. 245° C.). |
| 2-amino-3-methylaminopyrazine | ethyl 8-methylaminoimidazo[1,2-a]pyrazine-2-car- |

TABLE II-continued

| | |
|---|---|
| 2-amino-5-bromo-3-methyl-aminopyrazine | boxylate (m.p. 184° C.). ethyl 6-bromo-8-methylamino-imidazo[1,2-a]pyrazine-2-carboxylate (m.p. 234° C.). |
| 2-amino-5-bromo-3-ethyl-aminopyrazine | ethyl 6-bromo-8-ethylamino-imidazo[1,2-a]pyrazine-2-carboxylate (m.p. 180° C.). |
| 2-amino-3-propylaminopyrazine | ethyl 8-propylaminoimidazo-[1,2-a]pyrazine-2-carboxylate (m.p. 145° C.). |
| 2-amino-5-bromo-3-propyl-aminopyrazine | ethyl 6-bromo-8-propylamino-imidazo[1,2-a]pyrazine-2-carboxylate (m.p. 190° C.). |
| 2-amino-5-bromo-3-butyl-aminopyrazine | ethyl 6-bromo-8-butylamino-imidazo[1,2-a]pyrazine-2-carboxylate (m.p. 176° C.). |
| 2-amino-5-bromo-3-sec-butylaminopyrazine | ethyl 6-bromo-8-sec-butyl-aminoimidazo[1,2-a]pyrazine-2-carboxylate (m.p. 187° C.). |
| 2-amino-3-piperidylpyrazine | ethyl 8-piperidylimidazo-[1,2-a]pyrazine-2-carboxylate (m.p. 114° C.). |
| 2-amino-5-bromo-3-piperidylpyrazine | ethyl 6-bromo-8-piperidyl-imidazo[1,2-a]pyrazine-2-carboxylate (m.p. 134° C.). |
| 2-amino-3-morpholinylpyrazine | ethyl 8-morpholinylimid-azo[1,2-a]pyrazine-2-carboxylate (m.p. 155° C.). |
| 2-amino-5-bromo-3-morpholinylpyrazine | ethyl 6-bromo-8-morpholinyl-imidazo[1,2-a]pyrazine-2-carboxylate (m.p. 140° C.). |
| 2-amino-5-bromo-3-(2-hydroxyethylamino)pyrazine | ethyl 6-bromo-8-(2-hydroxyethylamino)imidazo[1,2-a]-pyrazine-2-carboxylate (m.p. 208° C.). |
| 2,3-diamino-5-bromopyrazine | ethyl 8-amino-6-bromoimidazo[1,2-a]pyrazine-2-acetate (m.p. 181° C.). |

EXAMPLE 4

5-Chloro-8-ethylaminoimidazo[1,2-a]pyrazine

Stage A: preparation of
5,8-dichlorimidazo[1,2-a]pyrazine

This derivative is obtained according to a technique identical to that of Example 1, stage A, by replacing 2-aminopyrazine by 2-amino-3,6-dichloropyrazine. 2.4 grams (18.6 mmol) of this compound yield 1 g (Yld=37%) of 5,8-dichloroimidazo[1,2-a]pyrazine (m.p. 102° C.).

Stage B: preparation of
8-ethylamino-5-chloroimidazo[1,2-a]pyrazine

A solution of 1.5 g (9.8 mmol) of 5,8-dichloroimidazo[1,2-a]pyrazine in 25 ml of a 40% strength aqueous ethylamine solution is maintained with stirring for 12 hours. After concentration under reduced pressure and chromatography on a silica column (eluant=ether), 5-chloro-8-ethylaminoimidazo[1,2-a]pyrazine (m.p. 94° C.), is obtained.

EXAMPLE 5

8-Amino-3,6-dibromoimidazo[1,2-a]pyrazine.

Stage A: preparation of
3,6,8-tribromoimidazo[1,2-a]pyrazine

A solution of 0.8 g (2.9 mmol) of 6,8-dibromoimidazo[1,2-a]pyrazine and 1.2 g of N-bromosuccinimide in 40 ml of chloroform is brought to reflux for two hours. After being cooled, the organic solution is treated with aqueous Na$_2$CO$_3$ solution. The chloroform phase is collected and then evaporated. 1 g -(Yld=97%) of 3,6,8-tribromoimidazo[1,2-a]pyrazine (m.p. 161° C.) is obtained.

Stage B: preparation of
8-amino-3,6-dibromoimidazo[1,2-a]pyrazine

A solution of 1 g (2.8 mmol) of 3,6,8-tribromoimidazo[1,2-a]pyrazine in 50 ml of ammoniacal alcohol heated to 120° C. for 5 hours in a 250-ml autoclave. After reaction and evaporation of the solvent, 0.8 g (Yld=98%) of 8-amino-3,6-dibromoimidazo[1,2-a]pyrazine (m.p.=246° C.) is obtained.

By replacing, in Example 5 above, stage B, ammoniacal alcohol by:

.methylamine, 3,6-dibromo-8-methylaminoimidazo[1,2-a]pyrazine (m.p. 229° C.) is obtained;

or ethylamine, 3,6-dibromo-8-ethylaminoimidazo[1,2-a]pyrazine (m.p. 131° C.) is obtained;

or morpholine, 3,6-dibromo-8-morpholinoimidazo[1,2-a]pyrazine (m.p. 141° C.) is obtained;

or furfurylamine, 3,6-dibromo-8-furfurylaminoimidazo[1,2-a]pyrazine (m.p. 143° C.) is obtained;

or piperidine, 3,6-dibromo-8-piperidylimidazo[1,2-a]pyrazine (m.p. 72° C.) is obtained.

EXAMPLE 6

6-Bromo-8-methylaminoimidazo[1,2-a]pyrazine-2-carboxamide.

A suspension of 0.470 g (1.57 mmol) of ethyl 6-bromo-8-methylaminoimidazo[1,2-a]pyrazine-2-carboxylate, obtained according to the process described in Example 3, in 50 ml of concentrated aqueous ammonia solution, is brought to reflux for 4 hours. After the mixture is cooled, the precipitate is drained, washed and dried. 0.160 g (Yld=40%) of 6-bromo-8-methylaminoimidazo[1,2-a]pyrazine-2-carboxamide (m.p. 312° C.) is obtained.

EXAMPLE 7

3,5,6-Trichloro-8-methylamino-N-methylimidazo[1,2-a]pyrazine-2-carboxamide

Stage A: preparation of ethyl
imidazo[1,2-a]pyrazine-2-carboxylate

This derivative is obtained according to the technique described in Example 3, stage B, by reacting 2-aminopyrazine and ethyl bromopyruvate. Ethyl imidazo[1,2-a]pyrazine-2-carboxylate (m.p. 179° C., Yld=25%) is obtained.

Stage B: preparation of ethyl
3,5,6,8-tetrachloroimidazo[1,2-a]pyrazine-2-carboxylate 4 ml of sulfuryl chloride are added with stirring to a suspension of 0.720 g (3.77 mmol) of ethyl imidazo[1,2-a]pyrazine-2-carboxylate in 10 ml of anhydrous benzene, and the mixture is then brought to reflux for one hour. The solvent is then evaporated off under reduced pressure. The residue is poured onto ice, and then extracted after alkalinization. A mixture of 0.750 g (70%) of ethyl trichloroimidazo[1,2-a]pyrazine-2-carboxylate, m.p. 132° C., and 0.350 g (30%) of ethyl 3,5, 6,8-tetrachloroimidazo[1,2-a]pyrazine-2-carboxylate (m.p. 171° C.) is thereby obtained, and these are separated by chromatography on a silica column (eluant=dichloromethane to which 2% of methanol has been added).

Stage C: preparation of 8-methylamino-3,5,6-trichloro-N-methylimidazo[1,2-a]pyrazine-2-carboxamide 0.330 g (0.1 mmol) of ethyl 3,5,6,8-tetrachloroimidazo[1,2-a]pyrazine-2-carboxylate, obtained according to the above method, is dissolved at room temperature and with stirring in 20 ml of a concentrated aqueous methylamine solution. After extraction with dichloromethane, 0.296 g (96%) of 8-methylamino-3,5,6-trichloro-N-methylimidazo[1,2-a]pyrazine-2-carboxamide, m.p.262° C. and 0.02 g of ethyl 8-methylamino-3,5,6-trichloroimidazo[1,2-a]pyrazine-2-carboxylate are isolated.

EXAMPLE 8

6-Bromo-8-methylaminoimidazo[1,2-a]pyrazin-2-amine 0.42 g of bromine (8 mmol) is added to a solution, cooled with a mixture of ice and salt, of 1.9 g of NaOH (47.5 mmol) in 10 ml of water. After the addition of 1.62 g (6 mmol) of 6-bromo-8-methylaminoimidazo[1,2-a]pyrazine-2-carboxamide (obtained according to Example 6), the mixture is brought to reflux for half an hour. After the mixture is cooled, the precipitate formed is collected and the mother liquors are evaporated to dryness. These two fractions are treated with 10% strength HCl until the evolution of gas has ceased. The acid solution is then alkalinized. Extraction with dichloromethane gives 6-bromo-8-methylaminoimidazo[1,2-a]pyrazin-2-amine.

EXAMPLE 9

6-Bromo-8-methylamino-2-phenylimidazo[1,2-a]pyrazine

Stage A: preparation of 6,8-dibromo-2-phenylimidazo[1,2-a]pyrazine

This derivative is obtained according to a technique identical to that of Example 2, stage A, by replacing bromoacetaldehyde dimethyl acetal by 1-bromoacetophenone. 10 g (39.5 mmol) of 3,5-dibromo-2-aminopyrazine yield 8.3 g (Yld=60%) of 6,8-dibromo-2-phenylimidazo[1,2-a]pyrazine (m.p. 254° C.).

Stage B: preparation of 6-bromo-8-methylamino-2-phenylimidazo[1,2-a]pyrazine This derivative is obtained according to a technique identical to that of Example 2, stage B, by replacing morpholine by concentrated aqueous methylamine solution. 6-Bromo-8-methylamino-2-phenylimidazo[1,2-a]pyrazine is obtained.

EXAMPLE 10

6-Bromo-2-chloromethyl-8-dimethylaminoimidazo[1,2-a]pyrazine

Stage A: preparation of 2-amino-5-bromo-3-dimethylaminopyrazine

This derivative is obtained according to a technique identical to that of Example 3, stage A, by replacing methylamine by a 40% aqueous dimethylamine solution. 5 g (19.8 mmol) of 2-amino-3,5-dibromopyrazine give 3.18 g (Yld=74%) of 2-amino-5-bromo-3-dimethylaminopyrazine (m.p.145° C.).

Stage B: preparation of 6-bromo-2-chloromethyl-8-dimethylaminoimidazo[1,2-a]pyrazine.

1.17 g (9.2 mmol) of 1,3-dichloroacetone is added dropwise to a solution of 2 g (9.2 mmol) of 2-amino-5-bromo-3-dimethylaminopyrazine. After 3 hours under reflux, the alcohol is evaporated off under reduced pressure and the residue taken up with water, alkalinized and extracted with dichloromethane. After purification by chromatography, 6-bromo-2-chloromethyl-8-dimethylaminoimidazo[1,2-a]pyrazine is obtained.

EXAMPLE 11

6-Bromo-8-morpholinoimidazo[1,2-a]pyrazine-2-carbonitrile

Stage A: preparation of 6,8-dibromoimidazo[1,2-a]pyrazine-2-carboxamide

This derivative is obtained according to a technique identical to that described in Example 6, by replacing ethyl 6-bromo-8-methylaminoimidazo]1,2-a]prrazine-2-carboxylate by ethyl 6,8-dibromoimidazo[1,2-a]pyrazine2-carboxylate.

Starting with 3.5 g (10 mmol) of ester, 2.56 g of amide (Yld=80%) (m.p. 260° C.) are obtained.

Stage B: preparation of 6,8-dibromoimidazo[1,2-a]pyrazine-2-carbonitrile

A suspension of 1 g (3.1 mmol) of amide obtained in stage A above in 9 ml of phosphorus oxytribromide is brought to reflux for one hour. After dissolution, the excess POBr$_3$ is driven off by distillation. The residue is carefully poured onto ice. After alkalinization, extraction yields 0.6 g (63%) of 6,8-dibromoimidazo[1,2,-a]pyrazine-2-carbonitrile (m.p. 208° C.).

Stage C: preparation of 6-bromo-8-morpholinoimidazo[1,2-a]pyrazine-2-carbonitrile.

0.2 g (0.66 mmol) of nitrile is dissolved at room temperature and with stirring (one hour) in 3 ml of morpholine. After evaporation of the excess morpholine under reduced pressure, the residue is taken up with dichloromethane. The evaporated filtered solution yields 0.2 g (Yld=98%) of 6-bromo-8-morpholinoimidazo[1,2-a]pyrazine-2-carbonitrile (m.p. 265° C.).

The compounds which form the subject of the invention, as well as their pharmaceutically usable salts, possess pharmacological properties justifying their application in human or veterinary therapy. In particular, some derivatives proved to be endowed with greater antispasmodic, uterine relaxant, bronchodilatory and cardiac analeptic (inotropic and positive chronotropic function) activities than those of theophylline (Theo), chosen as reference constituent. It will be noted, in addition, that the compounds which form the subject of the present invention do not possess the neurostimulatory side effects of Theo and that, on the contrary, they prove to be endowed with neurosedative properties.

The demonstration of the pharmacological activities of some of the compounds of the present invention was carried out according to the tests described below. The test compounds are identified by a number corresponding to the structures specified in Table III below.

1. Antispasmodic activity

Fragments of duodenum are removed from male rats (200 g), fasted for 24 hours and killed by decapitation, and are mounted, after being washed, in a thermostatted (37° C.) isolated organ cell and maintained in survival in Tyrode's solution according to Magnus's classical technique.

The spasmogenic agent used is barium chloride ($10^{-4}$M).

In the first instance, the spasmogenic agent is added to the nutrient bath and, as soon as the contraction of the organ reaches its maximum, the relaxant agent is added to the medium. Working in relation to a fixed concentration of barium chloride with variable concentrations of relaxant, the $ED_{50}$ of the latter, capable of reducing the induced contraction by 50%, is determined.

The results expressed in Table IV below show the ratio $ED_{50}$ Theo/$ED_{50}$ product, established on the basis of the mean of the results of 5 to 6 determinations per product ($ED_{50}$ theophylline $= 8 \times 10^{-4}$M).

TABLE III

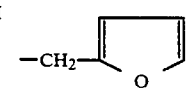

(I)

| Compound No. | Y | Z | $R_1$ | $R_2$ | $R_3$ | $R_4$ | M.p. (°C.) |
|---|---|---|---|---|---|---|---|
| 1 | H | H | H | H | H | H | 220 . |
| 2 | H | H | H | H | H | $CH_3$ | 96 . |
| 3 | H | H | H | H | H | $C_2H_5$ | 98 . |
| 4 | H | H | H | H | $-(CH_2)_2-O-(CH_2)_2-$ | | 127 . |
| 5 | H | H | H | Br | H | H | 239 |
| 6 | H | H | H | Br | H | $CH_3$ | 143 . |
| 7 | H | H | H | Br | H | $C_2H_5$ | 82 . |
| 8 | Br | H | H | H | H | H | 210 |
| 9 | Br | H | H | H | H | $CH_3$ | 162 . |
| 10 | Br | H | H | H | H | $C_2H_5$ | 99 |
| 11 | Br | H | H | H | $-(CH_2)_2-O-(CH_2)_2-$ | | 191 . |
| 12 | H | Cl | H | H | H | $C_2H_5$ | 94 |
| 13 | Br | H | H | Br | H | H | 246 . |
| 14 | Br | H | H | Br | H | $CH_3$ | 229 . |
| 15 | Br | H | H | Br | H | $C_2H_5$ | 131 . |
| 16 | Br | H | H | Br | $-(CH_2)_2-O-(CH_2)_2-$ | | 151 . |
| 17 | H | H | $CO_2Et$ | H | H | H | 230 . |
| 18 | H | H | $CO_2Et$ | H | H | $CH_3$ | 184 . |
| 19 | H | H | $CO_2Et$ | H | H | $C_3H_7$ | 145 . |
| 20 | H | H | $CO_2Et$ | H | $-(CH_2)_5-$ | | 114 . |
| 21 | H | H | $CO_2Et$ | H | $-(CH_2)_2-O-(CH_2)_2-$ | | 155 . |
| 22 | Br | H | $CO_2Et$ | H | H | H | 245 |
| 23 | Br | H | $CO_2Et$ | H | H | $CH_3$ | 234 |
| 24 | Br | H | $CO_2Et$ | H | H | $C_2H_5$ | 180 . |
| 25 | Br | H | $CO_2Et$ | H | H | $C_3H_7$ | 190 . |
| 26 | Br | H | $CO_2Et$ | H | H | n-$C_4H_9$ | 176 . |
| 27 | Br | H | $CO_2Et$ | H | H | s-$C_4H_9$ | 187 . |
| 28 | Br | H | $CO_2Et$ | H | $-(CH_2)_5-$ | | 134 . |
| 29 | Br | H | $CO_2Et$ | H | $-(CH_2)_2-O-(CH_2)_2-$ | | 140 . |
| 30 | Br | H | $CO_2Et$ | H | H | $-(CH_2)_2OH$ | 208 |
| 31 | Br | H | $CONH_2$ | H | H | $CH_3$ | 312 |
| 32 | Br | H | $CH_2CO_2Et$ | H | H | H | 181 . |
| 33 | Br | H | $CH_2CO_2Et$ | H | H | $CH_3$ | 104 |
| 34 | Cl | Cl | $CONHCH_3$ | Cl | H | $CH_3$ | 262 . |
| 35 | Br | H | $C{\equiv}N$ | H | $-(CH_2)_2-O-(CH_2)_2-$ | | 265 . |
| 36 | Br | H | H | H | H | $-CH_2-$furan | 164 . |
| 37 | Br | H | H | Br | H | $-CH_2-$furan | 143 . |
| 38 | Br | H | H | Br | $-(CH_2)_5-$ | | 72 . |
| 39 | H | H | H | H | H | $-CH_2-$furan | pasty |

TABLE IV

| Product | Antispasmodic activity ED$_{50}$ Theo/ED$_{50}$ product |
|---|---|
| 6 | 32 |
| 8 | 32 |
| 9 | 20 |
| 10 | 40 |
| 12 | 27 |
| 17 | 13 |

2. Uterine relaxant activity

Female rats (150–180 g) are killed by decapitation 24 hours after the intraperitoneal administration of stilbestrol (0.1 mg/kg). The uterine horns are removed and fragments mounted in a thermostatted (37° C.) isolated organ cell and maintained in survival in oxygenated De Jalon's solution of composition (mM): NaCl (153.8); KCl (5.6); CaCl$_2$ (2.16); NaHCO$_3$ (1.8); dextrose (5.5). One end of the uterine fragment is maintained fixed, while the other is attached to a recording myograph under a tension of the order of 0.5 g. The spontaneous uterine contractions are recorded on a kymograph. The organ is left at rest for 30 minutes and washed three times. The test products are introduced directly into the bath after being dissolved in De Jalon's solution, and the activity measured (ED$_{50}$) corresponds to the dose capable of reducing the magnitude of the spontaneous contractions by 50%.

The results expressed in Table V below show the ratio ED$_{50}$ Theo/ED$_{50}$ product, established on the basis of the mean of the results of 5 to 10 determinations per product. (ED$_{50}$ theophylline = 0.9 × 10$^{-3}$ M)

TABLE V

| Compound | Uterine relaxant activity ED$_{50}$ Theo/ED$_{50}$ product |
|---|---|
| 6 | 9 |
| 8 | 3 |
| 9 | 5.6 |
| 10 | 7.2 |
| 17 | 2.6 |

3. Antibronchospastic activity

3.1. Bronchospasm induced in guinea pigs

Guinea pigs of both sexes weighing between 400 and 600 g are anesthetized with ethyl carbamate (1.20/kg i.p.). After tracheotomy, the animal is placed under artificial respiration at a constant flowrate (Palmer pump 1 ml/100 g×60/min). A take-off at the tracheal cannula enables the volume of air to be gaged at each inhalation by means of a Marey drum. Bronchospasm is induced by intraveneous (jugular) administration of histamine. For each animal, the dose of histamine (8 to 12 μg/kg) inducing an increase in the recording trace equal to double its initial value is determined. The dose adopted should provide three identical responses at intervals of 10 minutes.

The test product is administered intraveneously and then, 30 seconds later, histamine is administered again. The measured ED$_{50}$ represents the dose which reduces the histamine-induced bronchoconstriction by 50%. Table VI below shows the ratio ED$_{50}$ Theo/ED$_{50}$ product, established on the basis of the mean of the results of 5 to 8 determinations per product (ED$_{50}$ Theo = 4.3 × 10$^{-5}$ M/kg).

| Product | ED$_{50}$ Theo ED$_{50}$ product | Product | ED$_{50}$ Theo ED$_{50}$ product |
|---|---|---|---|
| 5 | 2 | 23 | 1 |
| 6 | 2 | 24 | 1 |
| 8 | 4 | 25 | <1 |
| 9 | 5.4 | 26 | <1 |
| 10 | 2 | 27 | <1 |
| 11 | 1 | 28 | <1 |
| 13 | 3.5 | 29 | 1 |
| 14 | 1.9 | 30 | <1 |
| 15 | 1.6 | 31 | 1 |
| 16 | 1 | 32 | 1.6 |
| 17 | 1.1 | 33 | 1 |
| 18 | 1 | 34 | 1.2 |
| 19 | <1 | 35 | <1 |
| 20 | 1 | 36 | <1 |
| 21 | <1 | 37 | 1.4 |
| 22 | 1.5 | 38 | 1.1 |

3.2. Isolated guinea pig trachea

Guinea pigs of both sexes weighing on average 400 to 600 g are sacrificed, and the tracheas are removed and placed at 37° C. in an oxygenated environment (95% O$_2$–5% CO$_2$) in Krebs fluid of the following composition (mM): NaCl (116), MgSO$_4$ (1.2), KCl (3.7), CaCl$_2$ (2.6), KH$_2$PO$_4$ (2.2), NaHCO$_3$ (24.9), glucose (10). The tracheal segments are then mounted horizontally between two hooks, one of which is fixed to the base of the isolated organ cell and the other is attached to a myograph under a tension of 0.5 g. The organ is left at rest for one hour and is subjected to four washes. The contraction-inducing reagent (carbachol) is added at a concentration (10$^{-4}$M) greater than the concentration giving the maximum effect. After stabilization of the contractional effect, gradually increasing accumulative amounts of the test products are added to the cell. The bronchodilatory effect is measured as the percentage inhibition of the maximal contraction and EC$_{50}$ represents the concentration inhibiting this concentration by 50%.

Table VII below shows the ratio EC50 theophylline/EC$_{50}$ product, established on the basis of the mean of the results of 5 to 6 determinations by product (EC$_{50}$-Theo = 10$^{-3}$M).

TABLE VII

| Anti-contractional activity (trachea) | | | |
|---|---|---|---|
| Product | EC$_{50}$ Theo/EC$_{50}$ product | Product | EC$_{50}$ Theo/EC$_{50}$ product |
| 1 | 1.5 | 7 | 5 |
| 2 | <1 | 8 | 11.3 |
| 3 | 1 | 9 | 8.3 |
| 4 | <1 | 10 | 5 |
| 5 | 11 | 11 | <1 |
| 6 | 12.5 | 39 | <1 |

4. Cardiac activity (inotropic and chronotropic function)

Guinea pigs of both sexes weighing between 300 and 500 g are killed by decapitation. The hearts are rapidly removed and placed in an oxygenated environment (95% O$_2$–5% CO$_2$) in Chenoweth-Koelle's solution of the following composition (mM): NaCl (120), KCl (5.63), CaCl$_2$ (2.0), dextrose (9.7), MgCl$_2$ (2.0), NaHCO$_3$ (26.0). The right and left atria are then separated from the heart and mounted in an isolated organ cell. The right atrium beats spontaneously and the left atrium is electrically stimulated. The organs under a tension of 1 g are left at rest for two hours and washed every fifteen minutes.

The products are added directly to the nutrient bath. The right atrium is used for measuring the modifications of rate (chronotropic function) whereas the left atrium indicates the modifications brought about in the contractile force (inotropic function).

For the inotropic function, the concentration capable of producing an increase in magnitude of 0.5 g with respect to the basic contraction is measured.

For the chronotropic function, the concentration capable of producing a 20% increase in the basic value of the rate is determined.

Table VIII below shows the ratio of activity between theophylline and Product for these two parameters ED Theo/ED Product.

$$ED \text{ Theo} \quad \text{inotropic function} = 8 \times 10^{-4} M$$
$$\text{chronotropic function} = 4 \times 10^{-4} M$$

TABLE VIII

| Product | Cardiac activity | |
|---|---|---|
| | Inotropic function | Chronotropic function |
| 6 | 5 | 6 |
| 8 | 10 | 2 |
| 9 | 50 | 25 |
| 10 | 4 | 15 |
| 17 | <1 | <1 |

5. Motor activity

The measurement of the neurosedative effect is based on the test of activity measurements in mice. Male mice weighing on average 25 to 30 g receive 55 and 166 pmol/kg of the test products intraperitoneally, and the control animals receive the corresponding doses of the vehicle. Five minutes after the administration, the animals are placed in activity-measuring cages, which record their movements digitally by means of the interruption of beams of light. The results are recorded in Table IX and expressed as the percentage variation (increase or decrease ) in activity compared with the controls during a period of 50 minutes following the administration.

TABLE IX

| PRODUCT | spontaneous activity - % variation compared with the controls. | |
|---|---|---|
| | 55 μmol/kg | 166 μmol/kg |
| 6 | ↓ 25 | ↓ 57 |
| 8 | ↓ 53 | ↓ 83 |
| 9 | ↓ 74 | ↓ 83 |
| 10 | ↓ 13 | ↓ 73 |
| 17 | ↑ 28 | ↓ 17 |
| 23 | ↓ 43 | ↓ 56 |
| Theophylline | ↑ 130 | ↑ 170 |

Naturally, the results of the trials presented above have been given only by way of illustration of the pharmacological properties which may be possessed by the compounds of the invention. The latter may hence be combined with any suitable excipient customarily used in human or veterinary therapy for the purpose of preparing and presenting pharmaceutical compositions which may be administered in the field of application of antispasmodics, uterine relaxants, bronchodilators, cardiac analeptics and neuro-sedatives. Thus, these compositions may take conventional pharmaceutical or modified-release forms, intended for oral or parenteral administration or administration via the mucosal and cutaneous linings, and containing the desired dose of active agent.

Naturally, the dosage and the methods of administration will, for each case, be left to the judgment and decision of the treating practitioner.

It is self-evident that the present invention has been described only in purely explanatory fashion and without any implied limitation, and that any expedient modification may be applied thereto without departing from the scope thereof.

We claim:

1. An 8-aminoimidazo[1,2-a]pyrazine compound corresponding to formula (I) or a salt which is compatible with pharmaceutical application, which corresponds to the formula:

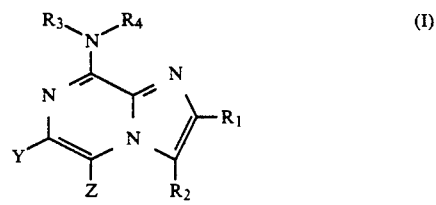

in which formula:
. Y and Z independently denote:
  a) a hydrogen atom,
  b) F, Cl, Br or I,
  c) $CO_2H$,
  d) CN,
  e) a linear or branched $C_1-C_5$ alkyl radical,
  f) a $C_1-C_5$ alkoxy radical,
  g) $CF_3$

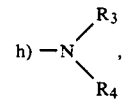

with $R_3$ and $R_4$ as defined below;
. $R_1$ and $R_2$, when they are independent, denote,
  a) a hydrogen atom,
  b) F, Cl, Br or I,
  c) a linear or branched $C_1-C_5$ alkyl radical,
  d) a radical $-(CH_2)_n-CO_2R_5$, with $R_5$ denoting a $C_1-C_5$ alkyl radical and n being from 0 to 4,

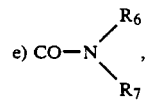

with $R_6$ and $R_7$ independently denoting a hydrogen atom, a linear or branched $C_1-C_5$ alkyl radical or an aryl radical,
f) CN,

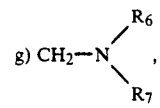

h) $NH_2$,
i) $CH_2Cl$, j) CH$_2$OH,
k) CF$_3$, l) SO$_2$—N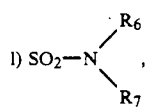

m) —NO$_2$,
n) —NO,
o) a C$_3$-C$_6$ cycloalkyl radical,
p) a linear or branched C$_1$-C$_5$ alkylthio radical;

. R$_1$ and R$_2$, when they are linked to one another, denote —CH$_2$—CH$_2$—CH$_2$—CH$_2$—, . R$_3$ and R$_4$ independently denote:
  a) a hydrogen atom
  b) a linear or branched C$_1$-C$_5$ alkyl radical, capable of bearing one or more halogen atoms or a hydroxy, N(C$_1$-C$_4$ alkyl)2, carbamoyl or C$_1$-C$_4$ alkoxy radical, either a C$_3$-C$_6$ cycloalkyl radical or a phenyl radical,
  c) a furfuryl radical, . R$_3$ and R$_4$, linked to one another denote —CH$_2$—CH$_2$—CH$_2$—CH$_2$—CH$_2$ or —CH$_2$—CH$_2$—X—CH$_2$—CH$_2$— in which X denotes O or S.

2. A compound as claimed in claim 1, which corresponds to the formula (I) in which R$_3$=H, R$_4$=H or a methyl or ethyl radical, R$_1$=H or an ethyl carboxylate group, Y and Z denote either H or Br and R$_2$ denotes Br or H.

3. A compound as claimed in claim 1, which corresponds to the formula (I) in which R$_3$=H, R$_4$=CH$_3$ or C$_2$H$_5$, Y=H, Z=H, R$_2$=Br and R$_1$=H, namely, a compound of one of the formula:

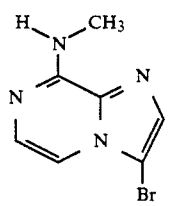 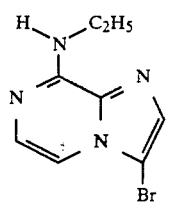

having, respectively, a melting point of 143° C. and 82° C.

4. A compound as claimed in claim 1, which corresponds to the formula (I) in which Y denotes a bromine atom and R$_1$, R$_2$, R$_3$, R$_4$ and Z denote hydrogen atoms, namely the compound of the formula

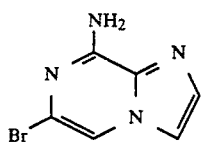

having a melting point of 210° C.

5. A compound as claimed in claim 1, which corresponds to formula (I) in which R$_3$=H, R$_4$=CH$_3$ or C$_2$H$_5$, Y=Br, Z=H, R$_2$=H, and R$_1$=H, namely: a compound of one of the formulae:

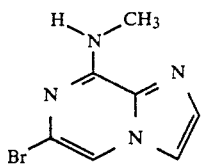 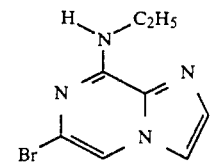

having, respectively, a melting point of 162° C. and 99° C.

6. A compound as claimed in claim 1, which corresponds to formula (I) in which R$_3$=H, R$_4$=H, Y=Br, Z=H, R$_2$=Br and R$_1$=H, namely the compound of the formula:

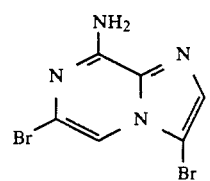

having a melting point of 246° C.

7. A compound as claimed in claim 1, which corresponds to formula (I) in which Y, Z, R$_1$, R$_2$, R$_3$ and R$_4$ denote hydrogen atoms, namely: the compound of the formula:

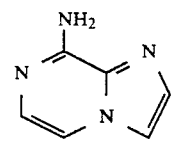

having a melting point of 220° C.

8. A compound as claimed in claim 1, which corresponds to formula (I) in which Y, Z, R$_1$, R$_2$ and R$_3$ denote hydrogen atoms and R$_4$ denotes a methyl or ethyl radical, namely: a compound of one of the formulae:

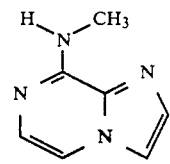

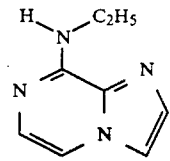

having, respectively, a melting point of 96° C. and 98° C.

9. A compound as claimed in claim 1, which corresponds to formula (I) in which Y, Z, R$_1$ and R$_2$ denote hydrogen atoms and R$_3$ and R$_4$ are linked to one another to denote a —(CH$_2$)$_2$—O—(CH$_2$)$_2$— radical, namely: the compound of the formula:

having a melting point of 127° C.

10. A compound as claimed in claim 1, which corresponds to formula (I) in which Y, Z, $R_1$, $R_3$ and $R_4$ denote hydrogen atoms and $R_2$ denotes a bromine atom, namely: the compound of the formula:

having a melting point of 239° C.

11. A compound as claimed in claim 1, which corresponds to formula (I) in which Y denotes a bromine atom, Z, $R_1$ and $R_2$ denote hydrogen atoms, and $R_3$ and $R_4$ are linked to one another to denote a —($CH_2$)$_2$—O—($CH_2$)$_2$— radical, namely: the compound of the formula:

having a melting point of 191° C.

12. A compound as claimed in claim 1, which corresponds to formula (I) in which Y, $R_1$, $R_2$ and $R_3$ denote hydrogen atoms, Z denotes a chlorine atom and $R_4$ denotes a $C_2H_5$ radical, namely: the compound of the formula:

having a melting point of 94° C.

13. A compound as claimed in claim 1, which corresponds to formula (I) in which Y and $R_2$ denote bromine atoms, Z, $R_1$ and $R_3$ denote hydrogen atoms, and $R_4$ denotes a methyl or ethyl radical, namely: a compound of one of the formulae:

having, respectively, a melting point of 229° C. and 131° C.

14. A compound as claimed in claim 1, which corresponds to formula (I) in which Y and $R_2$ denote bromine atoms, Z and $R_1$ denote hydrogen atoms and $R_3$ and $R_4$ are linked to one another to denote a —($CH_2$)$_2$—O—($CH_2$)$_2$— radical, namely: the compound of the formula:

having a melting point of 151° C.

15. A compound as claimed in claim 1, which corresponds to formula (I) in which Y, Z, $R_2$ and $R_3$ denote hydrogen atoms and $R_4$ is hydrogen or a —$CH_3$ radical or a —$C_3H_7$ radical, and $R_1$ denotes a —$CO_2C_2H_5$ group, namely: a compound one of the formulae:

having, respectively, a melting point of 230° C., 184° C. and 145° C.

16. A compound as claimed in claim 1, which corresponds to formula (I) in which Y, Z and $R_2$ denote hydrogen atoms, $R_1$ denotes —$CO_2C_2H_5$, and $R_3$ and R4 are linked to one another to denote either a —(CH2)5— radical or a —(CH2)2—O—(CH2)2— radical, namely: a compound, respectively, of one of the formulae:

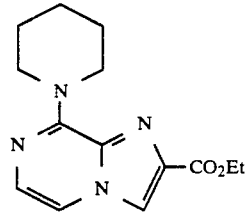

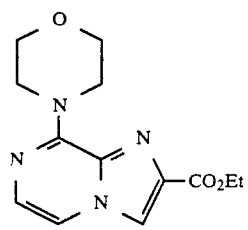

having, respectively, a melting point of 114° C. and 155° C.

17. A compound as claimed in claim 1, which corresponds to formula (I), in which Y denotes a bromine atom, Z, R3 and R2 denote hydrogen atoms, R1 denotes —CO2C2H5, and R4 denotes either a hydrogen atom or one of the radicals —CH3, —C2H5, —C3H7, n—C4H9, s—C4H9, namely: the compounds, respectively, of formula:

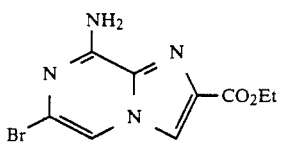

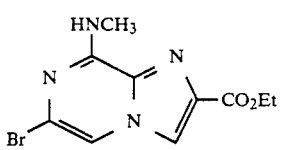

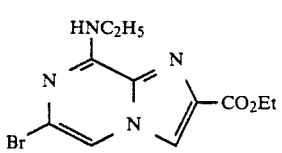

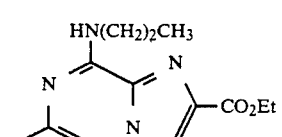

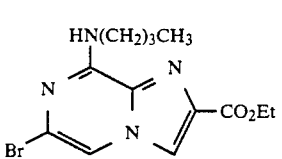

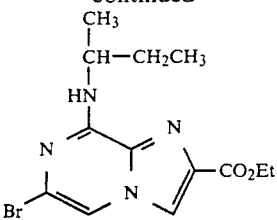

having, respectively, a melting point of 245° C., 234° C., 180° C., 190° C., 176° C. and 187° C.

18. A compound as claimed in claim 1, which corresponds to formula (I) in which Y denotes a bromine atom, Z and R2 denote hydrogen atoms, R1 denotes a —CO2C2H5 group and R3, and R4 are linked to one another to denote either a —(CH2)5-radical, or a —(CH2)2—O—(CH2)2-radical, namely: the compounds, respectively, of the formulae:

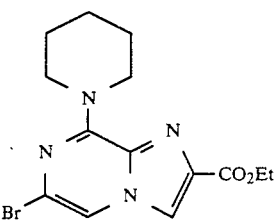

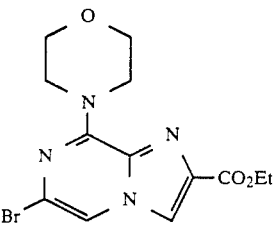

having, respectively, a melting point of 134° C. and 140° C.

19. A compound as claimed in claim 1, which corresponds to formula (I) in which Y denotes a bromine atom, Z, R2 and R3 denote hydrogen atoms, R4 denotes a —(CH2)2OH radical, and R1 denotes a —CO2C25 group, namely: the compound of the formula:

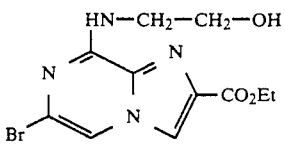

having a melting point of 208° C.

20. A compound as claimed in claim 1, which corresponds to formula (I) in which Y denotes a bromine atom, Z, R2 and R3 denote hydrogen atoms, R4 denotes a —CH3 radical and R1 denotes a —CONH2 group, namely the compound of the formula:

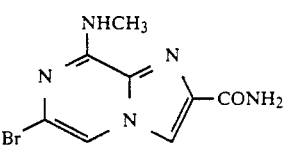

having a melting point of 312° C.

21. A compound as claimed in claim 1, which corresponds to formula (I) in which Y denotes a bromine atom, Z, $R_2$ and $R_3$ denote hydrogen atoms, $R_1$ denotes —$CH_2CO_2C_2H_5$, and $R_4$ denotes either hydrogen or a methyl radical, namely: the compounds, respectively, of the formulae:

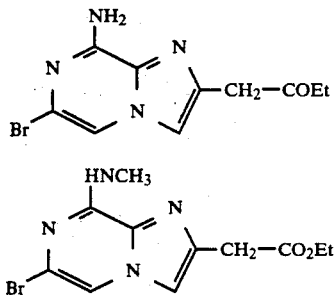

having, respectively, a melting point of 181° C. and 104° C.

22. A compound as claimed in claim 1, which corresponds to formula (I) in which Y, Z and $R_2$ denote chlorine atoms, $R_3$ denotes hydrogen, $R_4$ denotes a —$CH_3$ radical, and $R_1$ denotes a $CONHCH_3$ group, namely: the compound of the formulae:

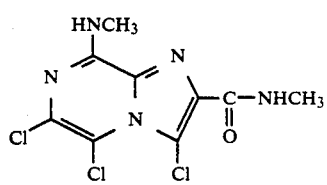

having a melting point of 262° C.

23. A compound as claimed in claim 1, which corresponds to formula (I) in which Y denotes a bromine atom, Z and $R_2$ denote hydrogen atoms, $R_1$ denotes a —CN radical, and $R_3$ and $R_4$ are linked to one another to denote a —$(CH_2)_2$—O— $(CH_2)_2$-radical, namely: the compound of the formula:

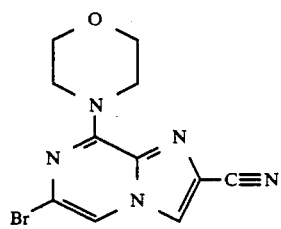

having a melting point of 265° C.

24. A compound as claimed in claim 1, which corresponds to formula (I) in which Y denotes a bromine atom, Z, $R_1$, and $R_3$ denote hydrogen atoms, $R_2$ denotes either a hydrogen atom or a bromine atom and $R_4$ denotes a

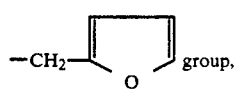

namely: the compounds, respectively, of the formulae:

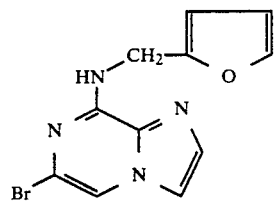

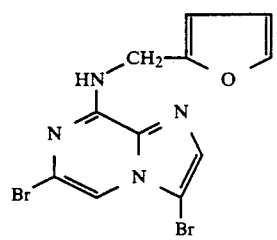

having, respectively, a melting point of 164° C. and 143° C.

25. A compound as claimed in claim 1, which corresponds to formula (I) in which Y and $R_2$ denote bromine atoms, Z and $R_1$ denote hydrogen atoms, and $R_3$ and $R_4$ are linked to one another to denote a $(CH_2)_5$-group, namely: the compound of the formulae:

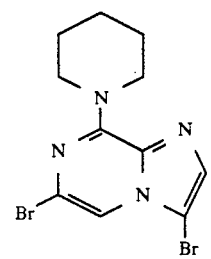

having a melting point of 72° C.

26. A compound as claimed in claim 1, in which Y, Z, $R_1$, $R_2$ and $R_3$ denote hydrogen atoms and $R_4$ denotes a

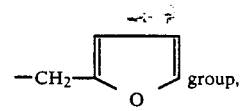

namely: the compound of the formulae:

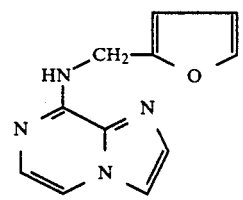

which compound is pasty.

27. A salt of a compound as claimed in claim 1, which results from the neutralization of a basic compound corresponding to formula (I) with a pharmaceutically acceptable.

28. A process of administering an antispasmodic, and uterine relaxant, a bronchodilator, a cardiac analeptic and/or composition, having an effective amount of active ingredient, to a human or other host in need of such therapy, wherein the active ingredient is a compound as claimed in claim 1 or a pharmaceutically-acceptable salt thereof.

29. A pharmaceutical antispasmodic, uterine, relaxant, bronchodilator, cardiac analeptic and/or sedative composition having an effective amount of a compound as claimed in claim 1 or of a pharmacologically-acceptable salt thereof in combination with pharmacologically-acceptable excipient.

30. A salt of claim 27 wherein the pharmaceutically-acceptable acid is a halogen hydracid, phosphoric acid, sulfuric acid, a carboxylic acid, isethionic acid or methanesulfonic acid.

* * * * *

UNITED STATES PATENT AND TRADEMARK OFFICE
CERTIFICATE OF CORRECTION

PATENT NO. : 5,028,605
DATED : June 2, 1991
INVENTOR(S) : SABLAYROLLES

It is certified that error appears in the above-identified patent and that said Letters Patent is hereby corrected as shown below:

Title Page, line 1, Item [54] and Col. 1, line 1, "(1,2-A)" should read
--[1,2-a]--                     in formula (I) "$R_3$ N $R_4$" should read
--$R_3$-N-$R_4$--; Abstract, Item 57,         (I), "advantages" should read
--advantageous--. Column 1 line 47, delete "(h)" and, immediately
below "g)", insert --h)--; line 60, delete "(e)" and, immediately
below "d)", insert --e)--. Column 2, line 3, delete "(g)" and,
immediately above "h)", insert --g)--; line 14, delete "(1)" and,
immediately below "k)", insert --l)--; line 34, "-CH-" should
read -- -$CH_2$- --; line 35, $_2$-$CH_2$-$CH_2$-$CH_2$-$CH_2$" should read
-- -$CH_2$-$CH_2$-$CH_2$-$CH_2$- --; line 60, "slaicylic" should read
--salicylic--. Column 5, lines 1 to 6, delete "H-N ... Scheme 4".
Column 7, line 26, "dibromooyrazine" should read
--dibromopyrazine--. Column 17, line 36, "pmol" should read
--$\mu$mol--; line 43 "increase or decrease" should read
--increase ⁄ or decrease ↖--. Column 24, line 46, "-$CO_2C_{25}$" should
read -- -$CO_2C_2H_5$--. Column 26, line 66 "and" should read --an--;
line 68, "and/or" should read --and/or sedative--. Column 27,
line 5, "uterine," should read --uterine--.

Signed and Sealed this

Third Day of August, 1993

Attest:

MICHAEL K. KIRK

Attesting Officer

Acting Commissioner of Patents and Trademarks